(12) United States Patent
Iwasa et al.

(10) Patent No.: US 7,873,526 B2
(45) Date of Patent: Jan. 18, 2011

(54) MEDICAL REPORT PRODUCING APPARATUS, MEDICAL REPORT REFERENCING APPARATUS, AND METHOD FOR PRODUCING MEDICAL REPORT

(75) Inventors: Akira Iwasa, Nasushiobara (JP); Kenichi Niwa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1232 days.

(21) Appl. No.: 11/442,333

(22) Filed: May 30, 2006

(65) Prior Publication Data

US 2006/0271403 A1 Nov. 30, 2006

(30) Foreign Application Priority Data

May 30, 2005 (JP) ............................. 2005-157325

(51) Int. Cl.
*G06Q 10/00* (2006.01)
(52) U.S. Cl. .......................................... 705/2; 715/206
(58) Field of Classification Search .................. 705/30, 705/2–3; 715/206
See application file for complete search history.

(56) References Cited

U.S. PATENT DOCUMENTS

| | | | |
|---|---|---|---|
| 6,272,470 B1 | 8/2001 | Teshima | |
| 6,995,859 B1 * | 2/2006 | Silverbrook et al. | 358/1.18 |
| 7,000,186 B1 * | 2/2006 | Gropper et al. | 715/202 |
| 7,058,901 B1 * | 6/2006 | Hafey et al. | 715/792 |
| 7,386,462 B2 * | 6/2008 | Silva-Craig et al. | 705/2 |
| 2002/0133373 A1 * | 9/2002 | Silva-Craig et al. | 705/2 |
| 2003/0177446 A1 * | 9/2003 | Gropper et al. | 715/522 |
| 2005/0226405 A1 | 10/2005 | Fukatsu et al. | |

FOREIGN PATENT DOCUMENTS

| | | |
|---|---|---|
| JP | 10-79770 | 3/1998 |
| JP | 2003-296451 | 10/2003 |
| JP | 2005-301453 | 10/2005 |

OTHER PUBLICATIONS

U.S. Appl. No. 12/062,209, filed Apr. 3, 2008, Minakuchi, et al.
U.S. Appl. No. 12/422,405, filed Apr. 13, 2009, Futami, et al.

* cited by examiner

*Primary Examiner*—Gerald J. O'Connor
*Assistant Examiner*—H. Nguyen
(74) *Attorney, Agent, or Firm*—Oblon, Spivak, McClelland, Maier & Neustadt, L.L.P.

(57) ABSTRACT

A link corresponding range is identified in a string in a finding section of a medical report display screen. A content is specified and dragged and dropped onto the area in which link corresponding range is displayed. When the string is specified, address information on the content is attached to the string. At the same time, the string in the link corresponding range is identified and displayed. The present apparatus subsequently determines whether or not to display information related to the linked reference content. If a display instruction has been given, a protocol that allows the related information to be automatically acquired and displayed is embedded in the hyperlink. When report production is completed, a file is saved to finish the series of processing operations. The file is then transferred to, for example, a trace reading report production requester.

22 Claims, 17 Drawing Sheets

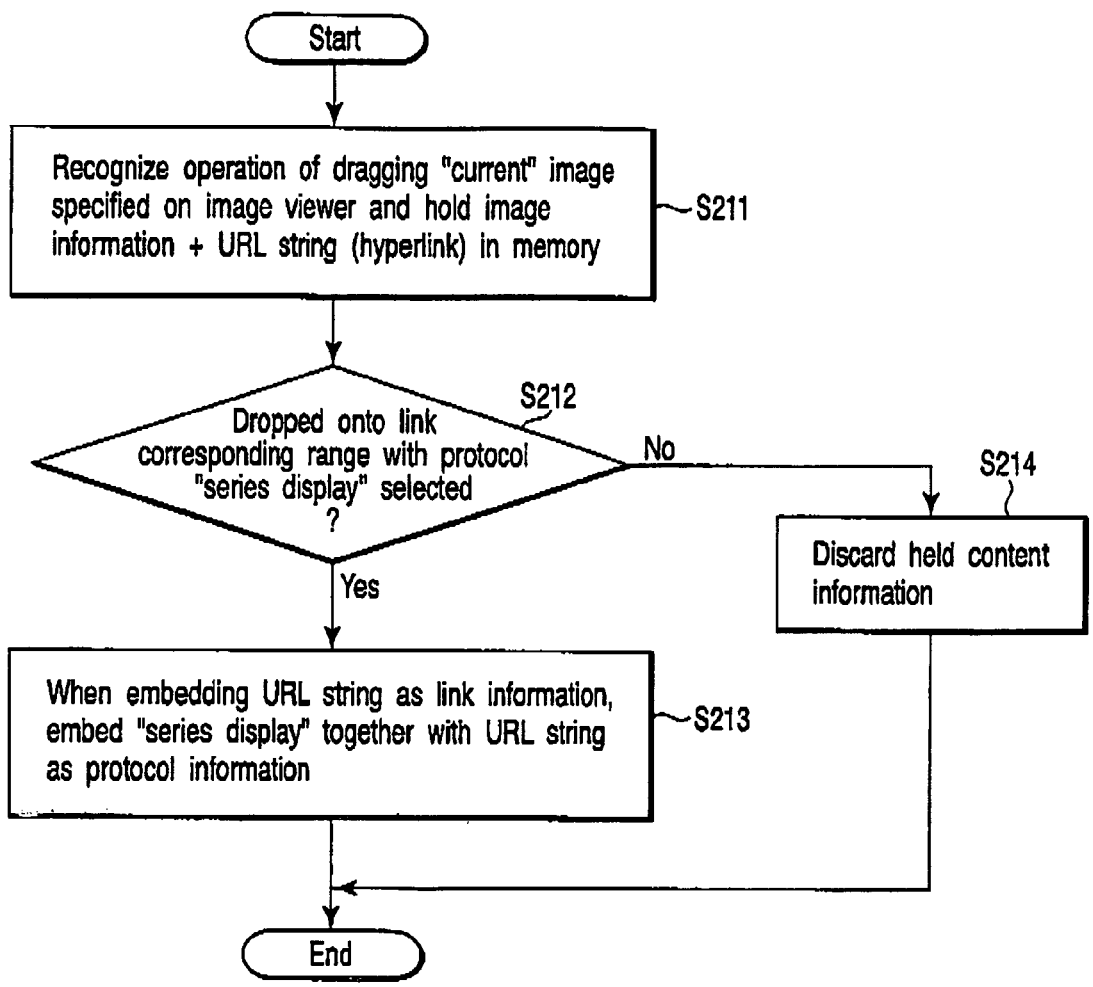
F I G. 8

| Key image status | A | B | C | D | E | F |
|---|---|---|---|---|---|---|
| Reconstruction process | – | – | MPR | – | Fusion | – |
| Modality | CT | CT | CT | CR | – | MR |
| Imaging site | Chest | Abdomen | Abdomen | Chest | – | Abdomen |
| Imaging condition | Lung field | – | – | – | – | T1 |
| Use of contrast | No | No | No | – | – | No |
| Related image display candidate | | | | | | |
| Comparison protocol number 1 | 1 | | 3 | | | |
| Comparison protocol number 2 | 6 | | 5 | | | |
| Comparison protocol number 3 | 7 | | 10 | | | |
| Comparison protocol number 4 | 9 | | 11 | | 12 | |
| Comparison protocol number 5 | 13 | | | | | 14 |
| | | | | | Undefined | |
| Relationship between examples and figures | | | | | | |
| Priority display protocol-Example 1 | 7 (FIG. 9) | | | | | |
| Priority display protocol-Example 2 | 1 (FIG. 10) | | | | | |
| Priority display protocol-Example 3 | | | | 12 (FIG. 11) | | |
| Priority display protocol-Example 4 | | 11 (FIG. 12) | | | | |
| Priority display protocol-Example 5 | 13 (FIG. 13) | | | | Default display (FIG. 12) | |
| Priority display protocol-Example 6 | | | | | | 14 (FIG. 14) |

FIG. 22

| Comparison protocol number | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Reconstruction process | – | – | – | – | – | – | – | MPR | – | – | – | – | – | – |
| Modality | CT | CT | CT | CT | CT | CT | CT | CT | CT | CT | CT | CR | CT | MR |
| Imaging site | Chest | Chest | Abdomen | Abdomen | Abdomen | Chest | Chest | Abdomen | Chest | Abdomen | Abdomen | Chest | Chest | Abdomen |
| Imaging condition | Lung field | Mediastinum | – | – | – | Lung field | Lung field | – | Lung field | – | – | – | Lung field | T1 |
| Comparison display target | | | | | | | | | | | | | | |
| Related examination | CT | CT | CT | CT | CT | CT | CT | CT | CT | MR | PET | CR | CT | MR |
| Comparison target based on time series | Last | Last | Same | Last | Last | Same | Same | Last | Same | Recent | Recent | Last | Same | Same |
| Use of contrast | No | No | Yes | Yes | No | No | No | No | No | T1,T2 | No | – | No | T2,FLAIR |
| Comparison display | | | | | | | | | | | | | | |
| Reconstruction process | – | – | – | – | – | MPR | MPR | MPR | Positioning | – | Fusion | Temporal differential | MIP | – |
| Display direction | Same | Same | Same | Same | Same | Two orthogonal planes | Coronal section | Same | – | Same | In accordance with PET | – | Two orthogonal planes | Same |
| Display position | Same | Same | Same | Same | Same | Same | Same | Same | – | Same | Same | – | Same | Same |

FIG. 23

MEDICAL REPORT PRODUCING APPARATUS, MEDICAL REPORT REFERENCING APPARATUS, AND METHOD FOR PRODUCING MEDICAL REPORT

CROSS-REFERENCE TO RELATED APPLICATIONS.

This application is based upon and claims the benefit of priority from prior Japanese Patent Application No. 2005-157325, filed May 30, 2005, the entire contents of which are incorporated herein by reference.

BACKGROUND OF THE INVENTION

1. Field of the Invention

The present invention relates to a medical report producing apparatus that produces a report on trace reading (it is called interpretation of radiogram) of medical images that a medical specialist has been requested to trace-read, and in particular, to a technique for producing a hyperlink text that links together images, past medical reports, and other files which correspond to the contents of characters in findings in a report.

2. Description of the Related Art

As a conventional medical information system, a medical image storage system (system may be composed of a server and a plurality of NASs (Network Attached Storages) on a network) has been provided which receives images from a modality (image diagnosis technique such as X-ray, ultrasonic wave, CT, MRI, or nuclear medicine) to store, manage, and distribute them. The medical image storage system has been useful for diagnosis that utilizes medical images.

It has been common to subdivide technical fields for medical acts and to request medical specialists to trace-read medical images taken by an image diagnosis apparatus such as MRI. A medical specialist requested to trace-read medical images allows trace reading target images be displayed and then makes a report on trace reading and delivers it to the requester.

Apparatuses have already been put to practical use which electronically produce medical reports. For example, medical images delivered by a trace reading requester via network distribution or the like are stored in the apparatus. A report sheet is displayed on a screen and then filled out. The images to be trace-read are sequentially displayed. Findings for the images are then entered into a finding section of the sheet. A diagnosis is entered into a diagnosis section on the basis of the image findings taking the requester's examination purpose into account. For an image referred to in the findings, a reduced/enlarged or clipped image is produced and attached to an image attachment section or the like. The sheet data in a medical report produced in accordance with the above procedure is delivered to the trace reading requester through, for example, the network.

It has been pointed out that in a report produced by the conventional medical report producing apparatus, the relationship between the contents of the findings and the attached image is often difficult to understand. For example, if a plurality of similar images are referred to in the text of the findings, the images may be mistaken for others. Further, if the attached image is displayed on a report screen, finding information may not be accurately communicated depending on monitor resolution or the size of a screen space. Furthermore, if not only images to be trace-read but also past medical reports or historical information are to be referenced, the specialist must perform a cumbersome operation of reading, editing, and attaching appropriate information file to the report.

It has thus been proposed that images displayed on a viewer be linked to characters on the report so that the apparatus can cooperate with an image server in displaying address information indicating where the images are stored, as a hyperlink text (see, for example, Jpn. Pat. Appln. KOKAI Publication No. 2005-301453). However, this technique can display only the information in the hyperlink text. If there are related images or newly processed images, the report producer must voluntarily re-link these pieces of information.

The requester may actually request to view a part or the whole of the process executed by a trace reading specialist. For example, the requester particularly desires to see images compared with one another during trace reading. To meet this requirement, the report producer must always carefully set up links, which increases the amount of work for report production.

Jpn. Pat. Appln. KOKAI Publication No. 10-079770 provides a technique for utilizing link information for referencing a particular group of files as external information in order to allow diagnostic information to be shared in an electronic medical report system. However, the technique described in this document only allows any medical institutions to draw a particular file group out of the link information stored in a submitted patient card. This technique cannot be simply utilized for the above medical report production.

As described above, the following function has been proposed for the conventional medical report producing apparatus in order to make the contents of findings easily understood: reference information is linked to a target position in a finding string so that the information can be displayed on the viewer by specifying and inputting a link destination. However, when many pieces of information are to be referenced, they must be sequentially linked together during report production. This disadvantageously requires a cumbersome report producing operation.

BRIEF SUMMARY OF THE INVENTION

An object of the present invention is to provide a medical report producing apparatus, a medical report referencing apparatus, and a method for producing a medical report which, during production of a trace reading report on medical images, enables automatic linking of information such as the medical images to be trace-read which information is contained in findings and expected to be referenced, so that a simple operation enables the information to be accurately communicated to the requester in an easy-to-understand manner.

A medical report producing apparatus according to the present invention produces an electronic file for a trace reading report on one or more medical images to be trace-read, and comprises information processing means for producing the electronic file for the medical report on the basis of information input in accordance with an operator's operation, first display means for displaying a production screen for the medical report produced by the information processing means, and second display means for selectively displaying at least one of contents including a medical image, a past medical report, and an information file which contents are referenced in order to produce the medical report. The information processing means comprises string input means for inputting a string to a finding section of the medical report, range identifying means for identifying a link corresponding range in the string in the finding section, linking process means for acquiring address information on the content in response to a specification input for the content displayed on the second display means, and linking the address information to the string information in the link corresponding range to produce a hyperlink text, and protocol input means for containing, in the hyperlink text, a protocol which executes a supplementary process associated with the linking target in accordance with the operator's instruction input.

A medical report referencing apparatus according to the present invention comprises display means for displaying a medical report containing a string to which address information on at least one of contents including a medical image, a past medical report, and a patient information file as well as a protocol allowing a process associated with the contents to be executed are linked as a hyperlink text, input means for specifying the linked string in a finding section of the medical report, and control means for referencing the hyperlink text linked to the specified string and acquiring the content on the basis of the address information, and allowing the content to be displayed in accordance with the protocol.

A method for producing a medical report according to the present invention produces an electronic file for a medical report on one or more medical images to be trace-read, and comprises allowing a production screen for a medical report to be displayed on the basis of the electronic file and also allowing selective display of one of contents including a medical image, a past medical report, and an information file which are referenced in order to produce the medical report, inserting a string input by an operator's operation into a finding section of the medical report, identifying a link corresponding range in the string in the finding section, acquiring address information on the content in response to a specification input for the content being displayed, and linking the address information to the string information in the link corresponding range to produce a hyperlink text, and containing, in the hyperlink text, a protocol which executes a supplementary process associated with the linking target in accordance with the operator's instruction input.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 8 is a flowchart showing a process procedure in Example 2 in which the medical report producing apparatus embeds protocol information;

FIG. 22 is a diagram showing a table for an optimum protocol selection logic that allows an optimum protocol to be automatically selected in order to link contents together;

FIG. 23 is a diagram showing a table containing comparison protocol numbers specified by the optimum protocol selection logic.

DETAILED DESCRIPTION OF THE INVENTION

Embodiments of the present invention will be described below in detail with reference to the drawings.

Figure 1:
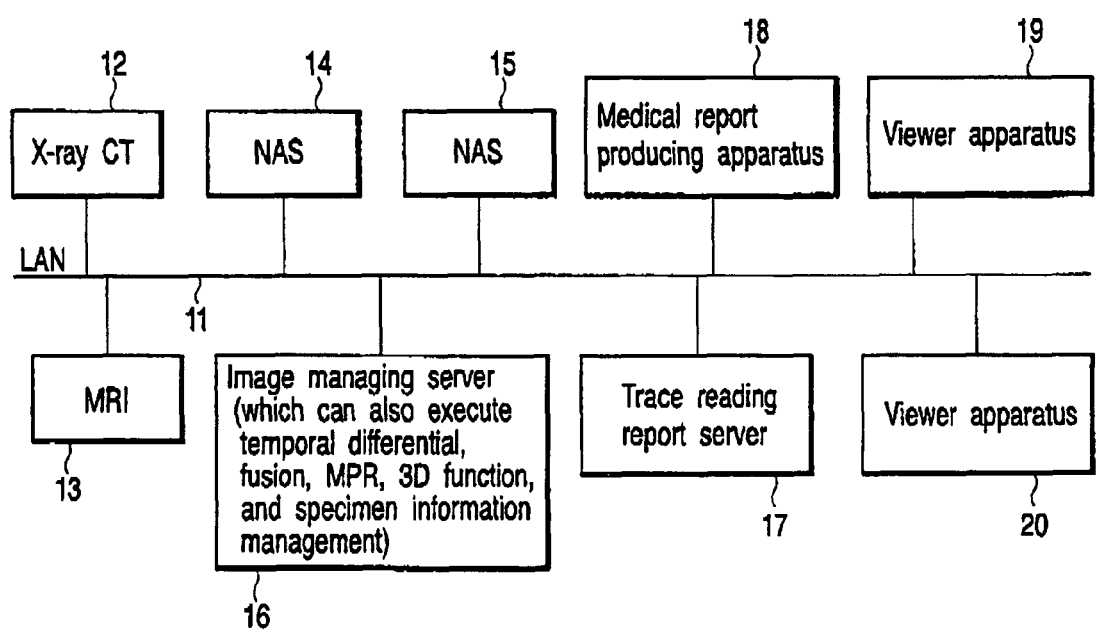
FIG. 1 is a block diagram showing the configuration of a hospital information system (HIS) including a medical report producing apparatus and a medical report referencing apparatus according to the present invention.

FIG. 1 is a block diagram showing the configuration of a hospital information system (HIS) including a medical report producing apparatus according to the present invention. In FIG. 1, reference numeral 11 denotes a local network (LAN) installed in a hospital. LAN 11 includes an X-ray CT (Computed Tomography) apparatus 12 or an MRI (Magnetic Resonance Imaging) apparatus 13, NASs (Network Attached Storages) 14 and 15, an image managing server 16, and a trace reading report server 17. LAN 11 further includes a medical report producing apparatus 18 comprising a viewer and a finding input device, and a plurality of viewer apparatuses 19 and 20 that allow a report to be viewed in an arbitrary place.

The image managing server 16 comprises the functions of appropriately records images acquired by the X-ray CT apparatus 12 or MRI apparatus 13, in NAS 14 or 15 or the like and executing temporal differential, fusion, MPR (Multi-Planar Reconstruction), or 3D display conversion on the images as well as specimen information management.

The trace reading report server 17 cooperates with the report producing apparatus 16 in supporting production of a trace reading report. The trace reading report server 17 has a function of supporting linking of a reference image or the like based on the contents of a report during its production.

Figure 2:
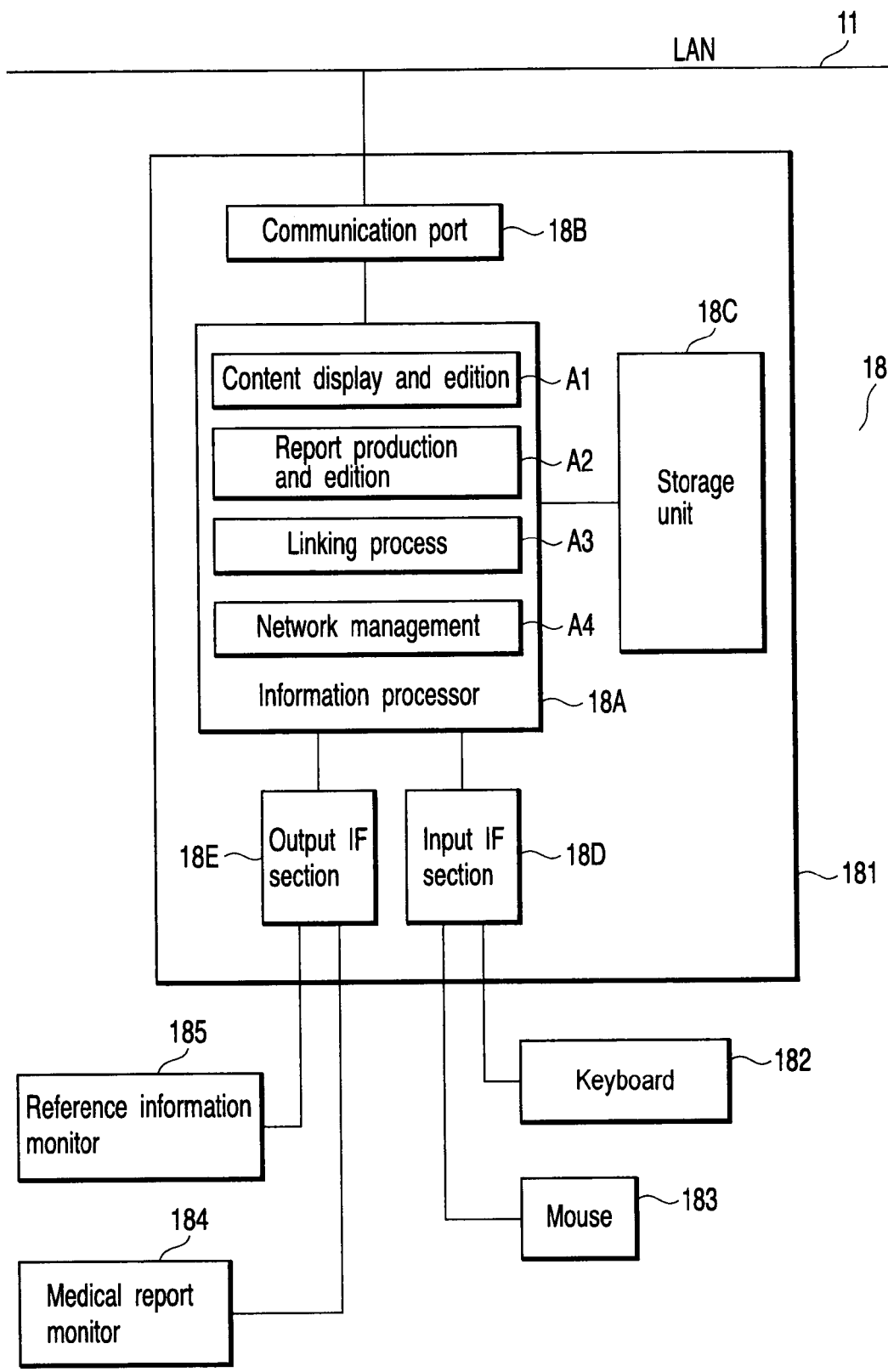
FIG. 2 is a block diagram showing an embodiment of a medical report producing apparatus according to the present invention.

In the hospital information system configured as described above, the medical report producing apparatus 18 according to the present invention is composed of an information processor 18A, a communication port 18B, a storage unit 18C in which information is stored for operations, an input interface section 18D that receives instruction information corresponding to an input operation via a keyboard 182 and a mouse 183, and a workstation device 181 comprising an output interface section 18E that outputs monitor display information to a report monitor device 184 and a reference information monitor device 185 as shown in FIG. 2. The storage unit 18C may be a cache memory but may be used with a hard disk device.

The information processor 18A reads contents such as images, past medical reports, historical information which are referenced for findings, from the trace reading report server 17 via the communication port 18B. The information processor 18A stores these contents in the storage unit 18C. The information processor 18A comprises, as applications, a content displaying and editing program A1 that monitors various contents to perform editing operations such as enlargement, reduction, and clipping, a report file producing and editing program A2 that produces and edits an electronic file for a medical report, and a linking process program A3, and a network managing program A4. The information processor 18A selects and executes any of these programs in response to power-on and in accordance with the operator's instruction input.

With reference to the flowchart shown in FIG. 3, description will be given of a procedure of producing a report which is executed by the medical report producing apparatus 18 configured as described above.

Figure 3:
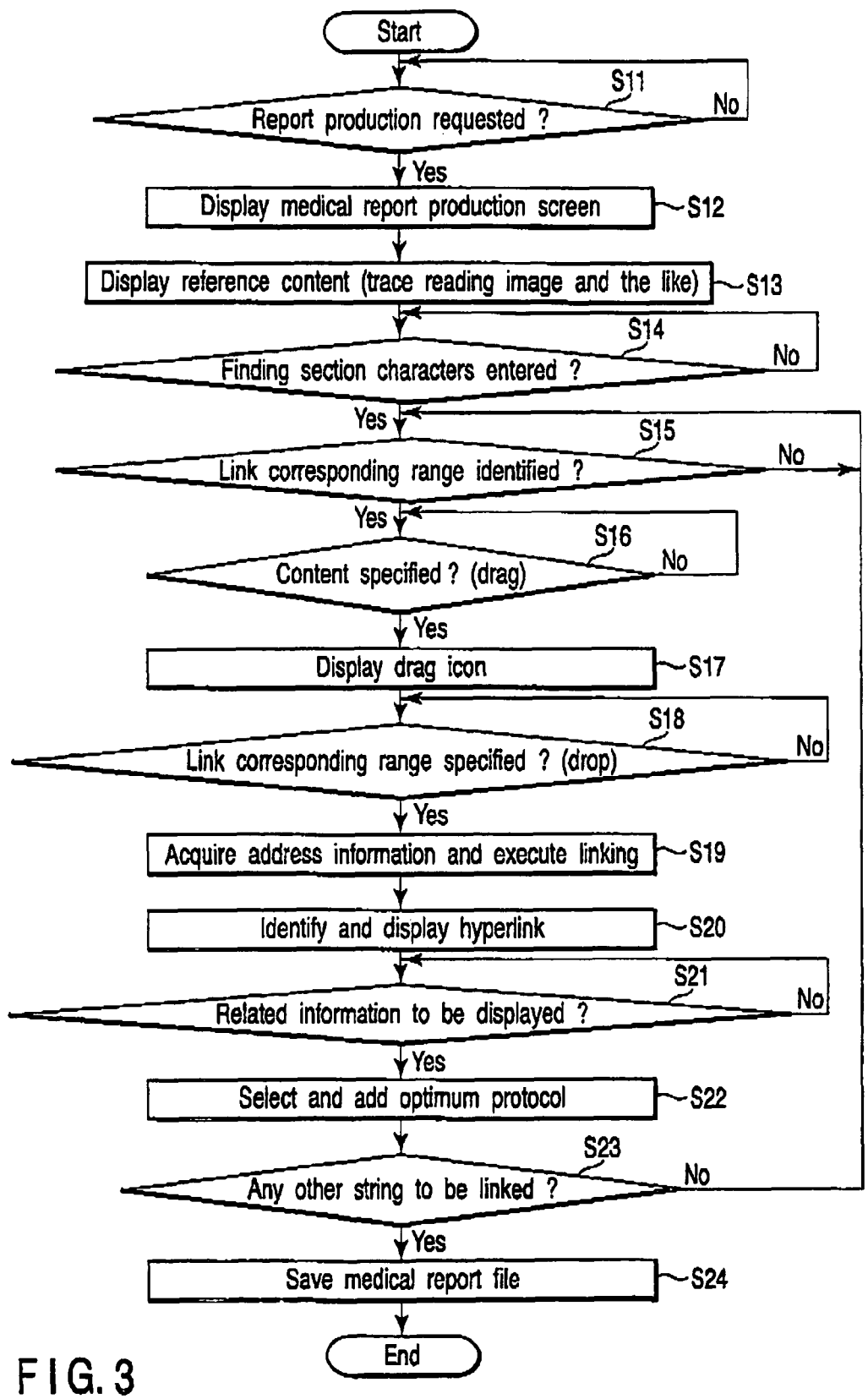
FIG. 3 is a flowchart showing a report producing procedure executed by the medical report creating apparatus shown in FIG. 2.

In FIG. 3, the apparatus first receives a request for production of a trace reading report on medical images, through the network 11 (step S11). The apparatus then displays a medical report production screen on the report monitor device 184 (step S12). The apparatus further displays an image requested to be trace-read, on the reference information monitor device 185 (step S13). In this case, the operator (report producer) basically enters bibliographic data in a medical report by operating the keyboard. However, the data in a request file may be automatically copied or pre-registered information may be selected and specified. Not only the trace reading request image but also contents to be referenced for findings may be appropriately read from the medical information server and displayed on the reference information monitor device 185; the contents to be referenced include, for example, past medical reports, diagnostic image, and historical information.

A finding section is provided in the medical report displayed on the monitor. When the operator performs an operation required to enter findings for the trace reading image in the finding section, the string input to the finding section is arranged (step S14).

With the string thus arranged, to link, to a particular string, the contents such as images, past medical reports, or historical information which are displayed on the reference information monitor device 185, the following procedure is executed in response to the operator's operation.

The apparatus first receives an operation of aligning a cursor with a string to be linked to identify a link corresponding range (step S15). The apparatus then receives an operation of dragging one of the contents being displayed on the monitor which is to be linked (step S16). At this time, the apparatus displays a drag display icon (step S17). The apparatus senses an operation of dropping the content onto a display portion showing the link corresponding range in the medical report production screen (step S18). When the string is specified, the apparatus acquires address information on the content from the image managing server 16. The apparatus then attaches the address information on the reference content to the string in hyperlink form (step S19). At the same time, the apparatus changes the color of the string in the link corresponding range for which the hyperlink has been 1S set and underlines the storing for identification (step S20).

The address information on the contents is expressed by:
http://[server host name or IP address]/DLink/ins.php?ins=1.2.3&ser=4.5.6&stu=7.8.9&Mod=MR&StuDat=yyyymmdd&PatID=abcde&param=xxxxxxxxxx
where ins: SOP instance UID,
ser: series instance UID,
stu: study instance UID,
Mod: modality,
StuDat: examination date,
PatID: patient ID, and
param: process parameters for the image (WW/WL, enlargement rate, clip position, and annotation information).

The apparatus subsequently determines whether or not to display information on the linked reference contents (step S21). If an instruction to display related information has been given, the apparatus selects and sets related information depending on the status of a content serving as a key. The apparatus selects an optimum protocol (described later in detail) that allows the related information to be automatically acquired from NAS 14 or 15, the image managing server 16, or the like and adds the protocol to the hyperlink (step S22).

The apparatus subsequently determines whether or not any other string is to link to the reference content (step S23). If any other string is to link to the reference content, the apparatus returns to the processing in step S15. If no other string is to link to the reference content, the apparatus determines that the input of the finding section string has been finished and saves the file (step S24) to complete the series of processing operations.

Figure 4:
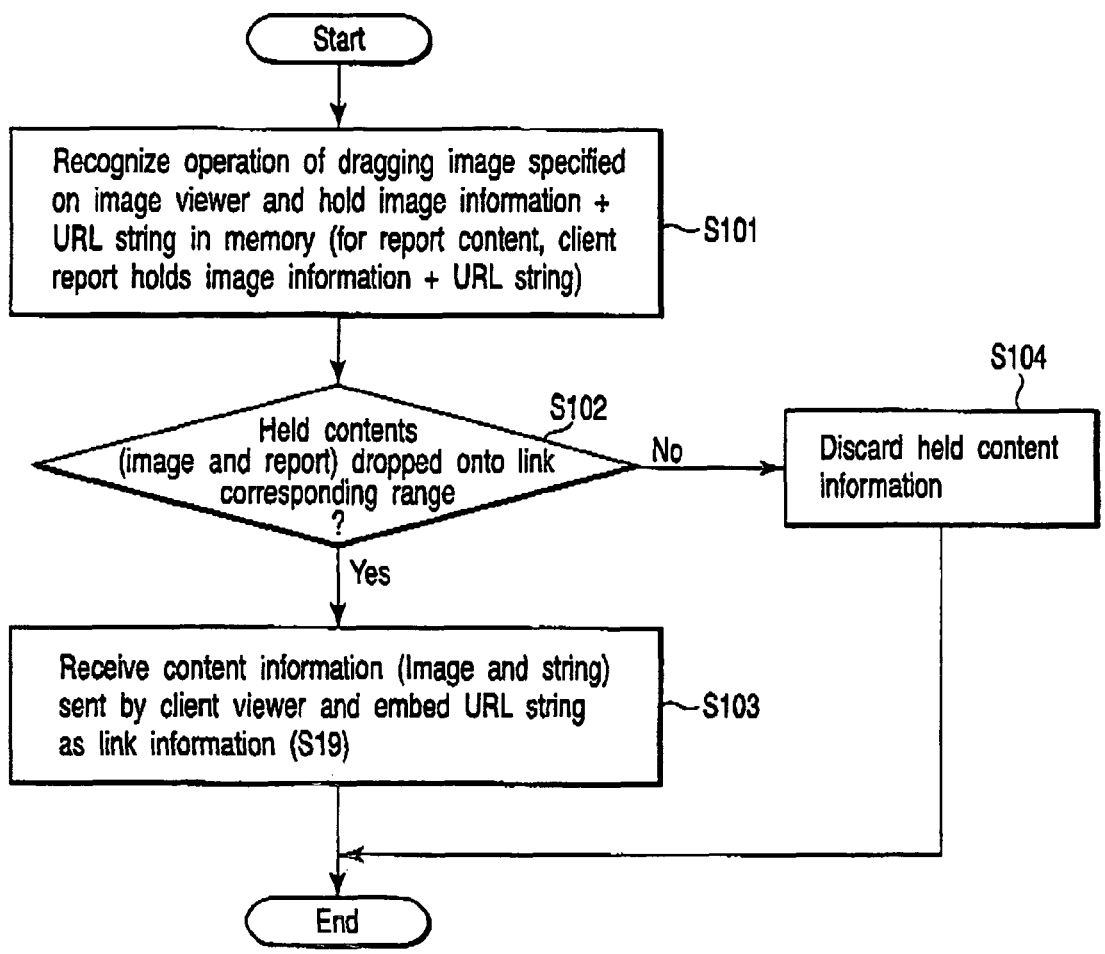
FIG. 4 is a flowchart showing a process procedure of attaching a link for contents to a medical report, the process procedure being included in the report producing procedure shown in FIG. 3.

With reference to the flowchart shown in FIG. 4, a supplementary description will be given of a process procedure of attaching a link for a content displayed on an image viewer (reference information monitor device 185) to a medical report displayed on a client viewer (report monitor device 184); the process procedure is included in the report producing procedure.

First, in step S16 shown in FIG. 3, an image specified on the image viewer is dragged to the client viewer, which then recognizes that drag operation and the image information and address information (URL string) in the memory (S101). If the content is a report, a client report application holds the report information and address information (URL string).

Figure 5B:
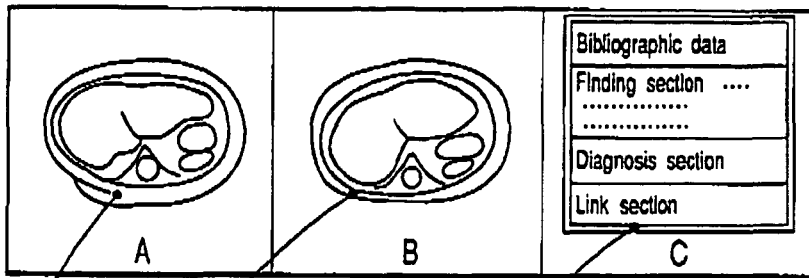
FIGS. 5A and 5B are diagrams showing a process of attaching a hyperlink via a drag drop operation of the medical report producing apparatus.
Figure 5A:
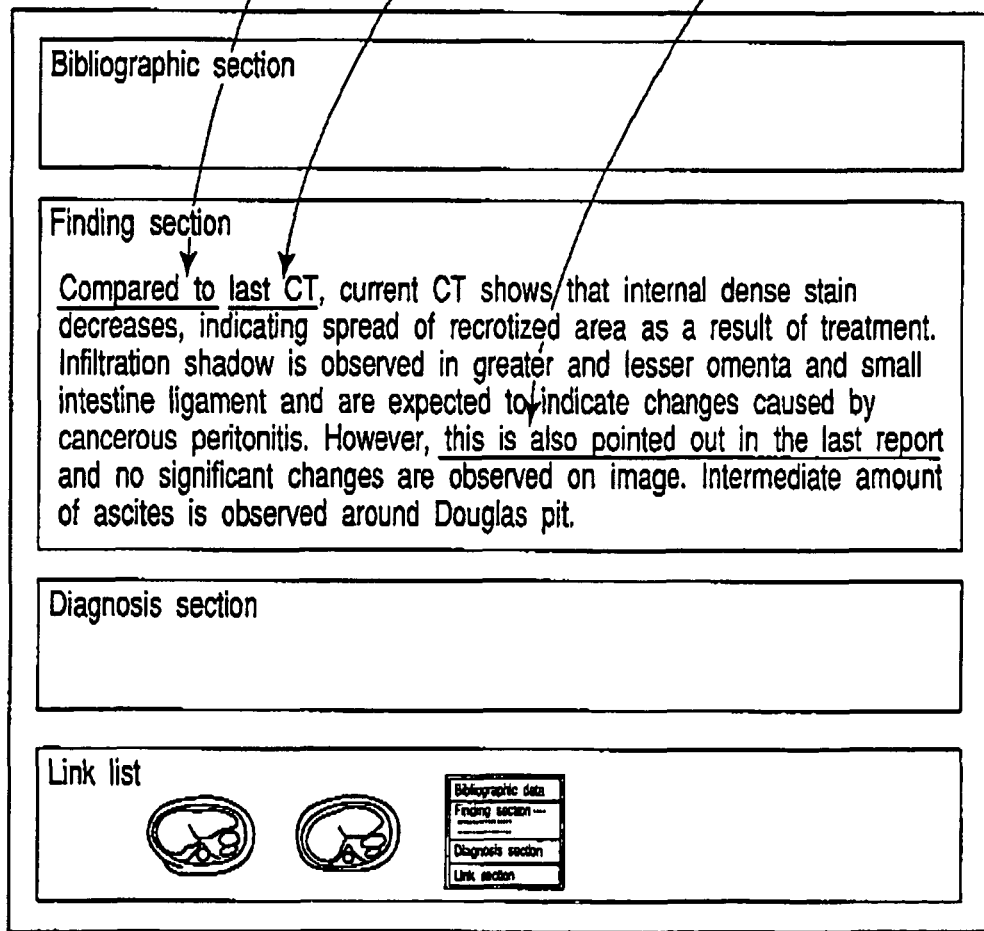

Then, in step S18 shown in FIG. 3, the client report application determines whether or not the held contents (images and report) have been dropped onto the link corresponding range (S102). If the contents have been dropped, then in step S19 shown in FIG. 3, the client report application receives the content information (image and string) sent by the client viewer. The client report application embeds the URL string in the content information as link information (S103) to finish the series of operations. In step S102, if the contents have not been dropped, the client report application discards the held content information (S104) to finish the series of operations. FIGS. 5A and 5B show how to attach a hyperlink via the drag and drop operation. FIG. 5A shows a medical report production screen, and FIG. 5B shows reference images A to C displayed on the monitor. The example of screen display in FIG. 5A shows a section in which bibliographic data such as the name, age, and medical history of the patient, an examination purpose, and imaging conditions is entered, a section in which findings are entered (finding section), a section in which a diagnosis is entered (diagnosis section), and a list of contents linked to the finding section (link list). The example of monitor display in FIG. 5B shows three reference images A, B, and C.

In this example, description will be given of linking of the reference image A to the part "tumor in both livers" in the string in the finding section. First, the operator identifies the string part "tumor in both livers" as a link corresponding range and drags and drops the reference image A onto this string part. This operation changes the color of the string part "tumor in both livers" and underlines it to indicate that a hyperlink has been attached to the string. On this occasion, dropping the reference image A onto the string part "tumor in both livers" allows address information on the reference image A to be acquired to attach a hyperlink for the address information to the corresponding string.

Figure 6:
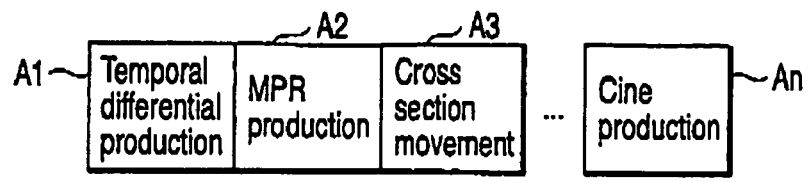
FIG. 6 is a view showing a function of the medical report producing apparatus for supporting protocol production by selecting, in blocks, procedures or image processing operations performed by a trace reading specialist and arranging them in accordance with a time series.

The present invention enables the hyperlink text itself to contain a protocol that operates like a macrofuncion to execute a supplementary process by performing predetermined instructing operations during execution of a program. The protocol may be, for example, a function of changing a display operation depending on the contents of content individual information such as the type of the linked images, the site, and the patient's ID, a function of searching for and displaying not only the linked images but also, for example, related images registered in the image managing server 16, or a function of checking the string in the hyperlink text for which the protocol is set. The protocol for producing a hyperlink text may be a function for helping protocol production by grouping procedures and image processing operations into functional blocks such as temporal differential production A1, MPR (Multi-Planar Reconstruction) production A2, cross section movement A3, . . . , cine production An, which are shown in FIG. 6, so that any of these blocks can be selected and arranged in accordance with the time series.

With the protocol produced, specifying and inputting a hyperlink text (click operation during a mouse cursor specification) allows an image to be automatically displayed. For example, display is carried out as described below.

EXAMPLE 1

If the "current" and "last" images are attached to the report, clicking either hyperlink display allows the corresponding two images to be automatically read and displayed so as to be arranged for easy comparison.

Figure 7:
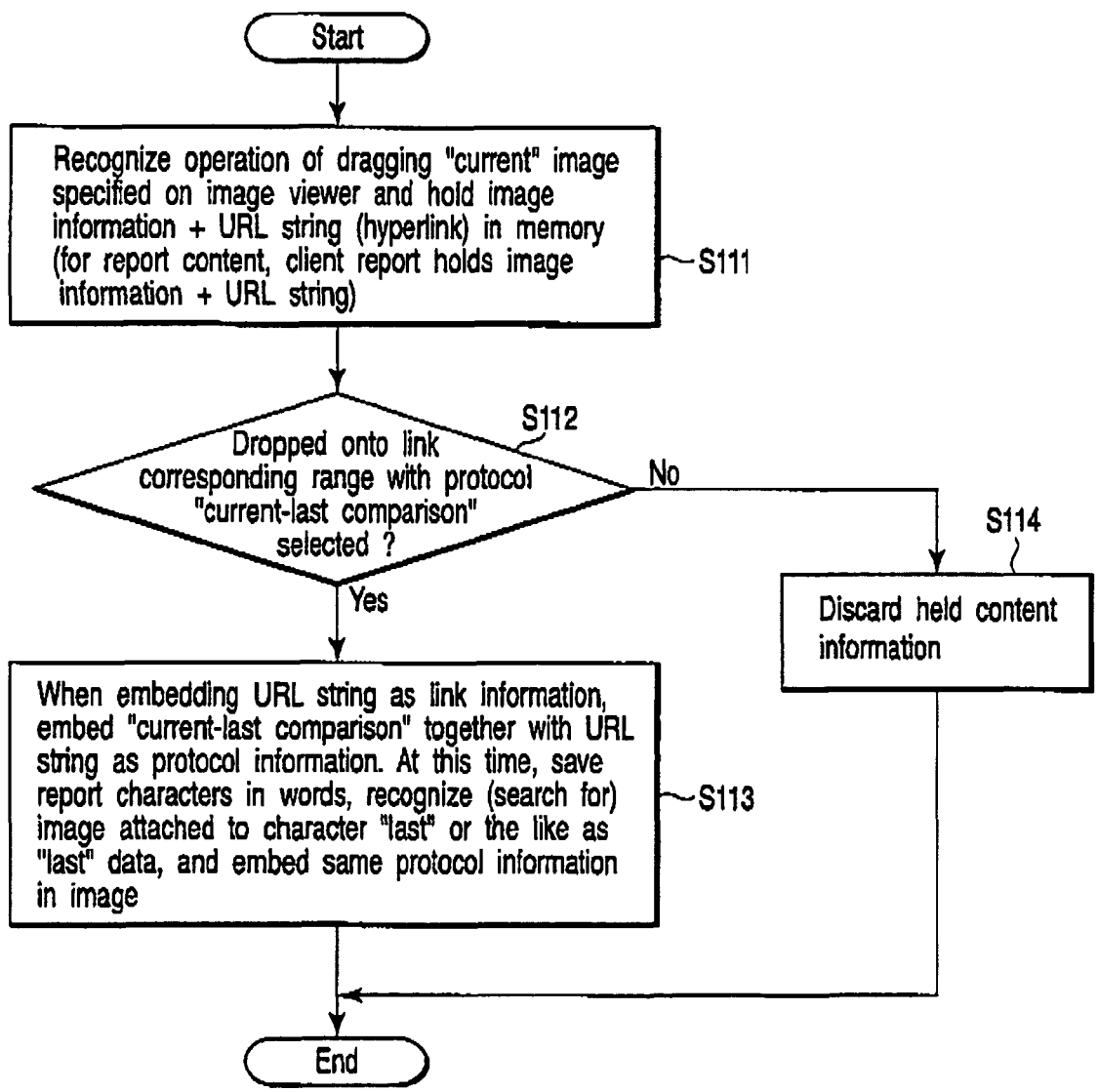
FIG. 7 is a flowchart showing a process procedure in Example 1 in which the medical report producing apparatus embeds protocol information.

FIG. 7 shows a process procedure in Example 1. In FIG. 7, first, the "current" image is specified on the image viewer and dragged to the client viewer. The client viewer application then recognizes the dragged image and holds the image information and URL string (hyperlink) in the memory (S111). The client report application then determines whether or not the contents have been dropped onto the link corresponding range with a protocol "current-last comparison" selected (S112). If the contents have been dropped under this condition, the client report application, when embedding the URL string as link information, additionally embeds the "current-last comparison" as protocol information. At this time, the client report application uses a technique such as text mining to save report characters in words. The client report application further recognizes (or searches for) the image attached to the character "last" as the last image and embeds the same protocol information in this image (S113) to finish the series of processing operations. In step S112, if the drop process has not been executed, the client report application discards the held content information (S114) to finish the series of processing operations.

An example of a URL string with the protocol information is "http://[server host name]/Dlink/ins.php?ins=1.2.3&Ser=4.5.6&stu=7.8.9&Mod=MR&StuDat=yyyymmdd&PatID=abcde&Param=XXXXXXX, Last-current comparison".

EXAMPLE 2

A series including a specified image can be automatically searched for and displayed. In this case, the first image to be displayed is the current selected image and the images preceding and following the current one are sequentially displayed as specified. This display form may be switched to a stack or tile display.

FIG. 8 shows a process procedure in Example 2. In FIG. 8, first, the "current" image is specified on the image viewer and dragged to the client viewer. The client viewer application then recognizes the dragged image and holds the image information and URL string (hyperlink) in the memory (S211). The client report application then determines whether or not the contents have been dropped onto the link corresponding range with a protocol "series display" selected (S212). If the contents have been dropped under this condition, the client report application, when embedding the URL string as link information, additionally embeds the "series display" as protocol information (S213) to finish the series of processing operations. In step S212, if the drop process has not been executed, the client report application discards the held content information (S214) to finish the series of processing operations.

An example of a URL string with the protocol information is "http://[server host name]/Dlink/ins.php?ins=1.2.3&Ser=4.5.6&stu=7.8.9&Mod=MR&StuDat=yyyymmdd&PatID=abcde&Param=XXXXXXX, Series display".

EXAMPLE 3

If the linked image is a CR (certain modality) image of the chest (certain site), the past images are searched for this chest image. If the past images contain the chest image, a temporal differential image is produced and automatically displayed.

Figure 9:
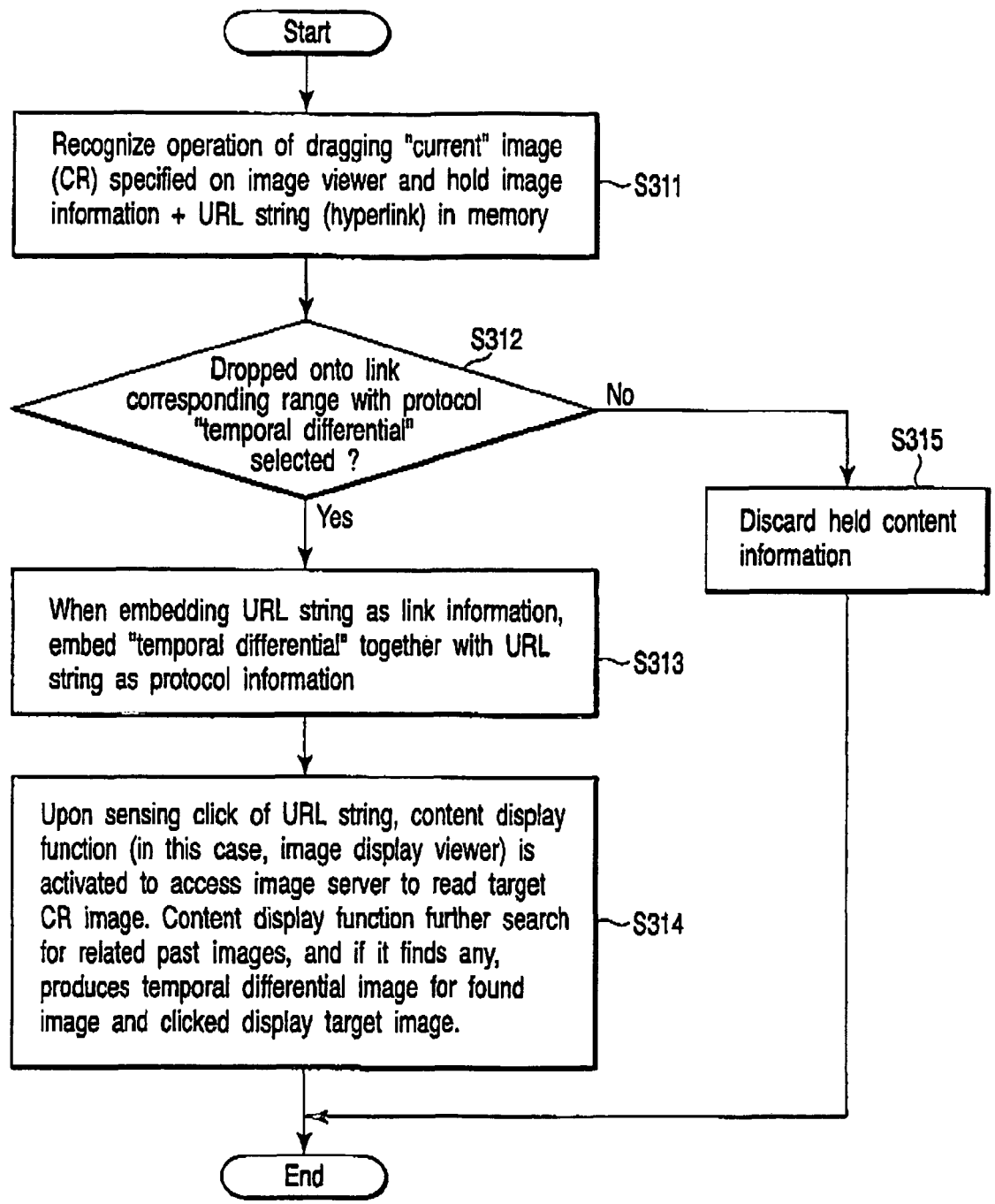
FIG. 9 is a flowchart showing a process procedure in Example 3 in which the medical report producing apparatus embeds protocol information.

FIG. 9 shows a process procedure in Example 3. In FIG. 9, first, the "current" image (CR) is specified on the image viewer and dragged to the client viewer. The client viewer application then recognizes the dragged image and holds the image information and URL string (hyperlink) in the memory (S311). The client report application then determines whether or not the contents have been dropped onto the link corresponding range with a protocol "temporal differential" selected (S312). If the contents have been dropped under this condition, the client report application, when embedding the URL string as link information, additionally embeds the "temporal differential" as protocol information (S313). Upon sensing a click of the URL string, the client report application activates a content display function (in this case, the image display viewer), which then accesses the image server to acquire and display the target CR image. The client report application further searches for related part images, and if it founds any, produces and displays a temporal differential image for the found image and display target image (S314). In step S312, if the drop process has not been executed, the client report application discards the held content information (S314) to finish the series of processing operations.

An example of a URL string with the protocol information is "http://[server host name]/Dlink/ins.php?ins=1.2.3&Ser=4.5.6&stu=7.8.9&Mod=MR&StuDat=yyyymmdd&PatID=abcde&Param=XXXXXXX, Temporal differential".

EXAMPLE 4

The apparatus determines whether or not the linked image contains any annotation information (graphic or textual information provided at a position of interest in an image for CRT display or diagnosis. Annotation information is utilized to clarify the position of findings or to add a comment to the report). If the report contains any annotation information, an MPR (Multi-Planar Reconstruction) display is automatically provided around that point.

Figure 10:
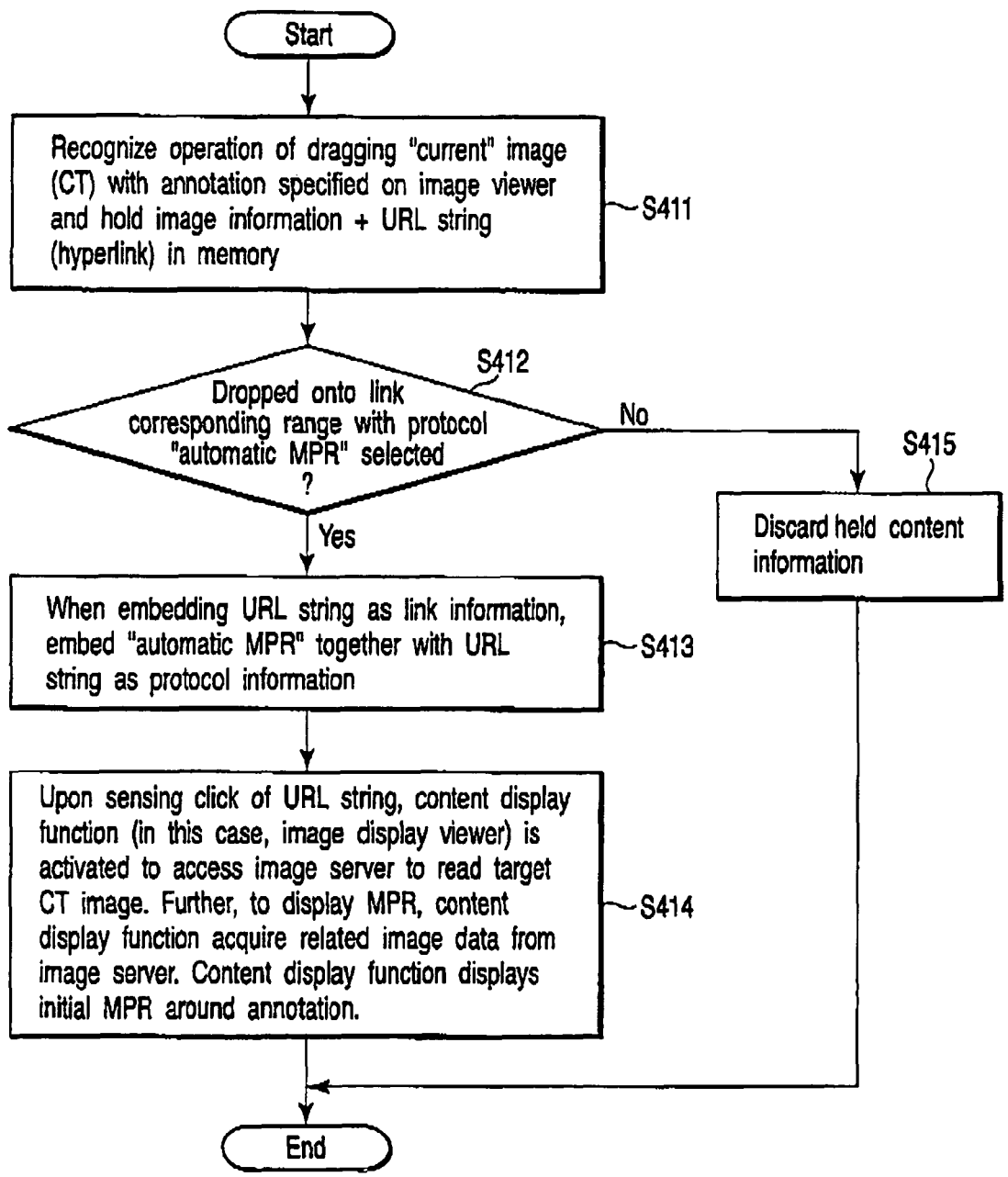
FIG. 10 is a flowchart showing a process procedure in Example 4 in which the medical report producing apparatus embeds protocol information.

FIG. 10 shows a process procedure in Example 4. In FIG. 10, first, the "current" image (CT) with an annotation is specified on the image viewer and dragged to the client viewer. The client viewer application then recognizes the dragged image and holds the image information and URL string (hyperlink) in the memory (S411). The client report application then determines whether or not the contents have been dropped onto the link corresponding range with a protocol "automatic MPR" selected (S412). If the contents have been dropped under this condition, the client report application, when embedding the URL string as link information, additionally embeds the "automatic MPR" as protocol information (S413). A click of the URL string allows the client report application to activate a content display function (in this case, the image display viewer), which then accesses the image server to acquire and display the target CT image. In order to display MPR, the content display function reads a related image from the image server. The content display function then displays initial MPR around the position of the annotation (S414). In step S412, if the drop process has not been executed, the client report application discards the held content information (S415) to finish the series of processing operations.

An example of a URL string with the protocol information is "http://[server host name]/Dlink/ins.php?ins=1.2.3&Ser=4.5.6&stu=7.8.9&Mod=MR&StuDat=yyyymmdd&PatID=abcde&Param=XXXXXXX, Automatic MPR".

Figure 16:
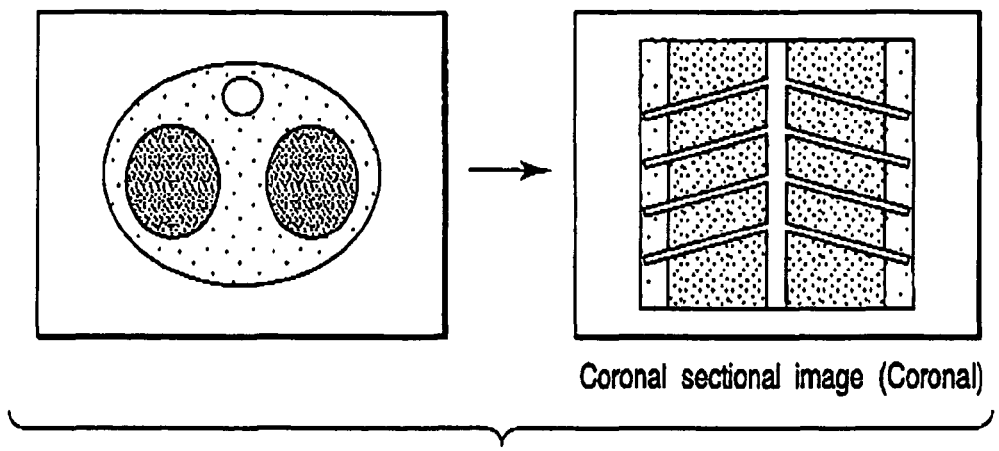
FIG. 16 is a diagram showing an example of the hyperlink image displayed when the hyperlink text is clicked.

Alternatively, as is understood from FIG. 23, described later, the protocol information may be a URL string such as "http://[server host name]/Dlink/ins.php?ins=1.2.3&Ser=4.5.6&stu=7.8.9&Mod=MR&StuDat=yyyymmdd&PatID=abcde&Param=XXXXXXX, 8". "8" indicates the contents of a protocol that provides such a display as shown in FIG. 16, described later.

EXAMPLE 5

The apparatus determines whether or not the linked image contains fusible (integrable) data, If the linked image contains fusible (integrable) data, a fused (integrated) display is provided.

Figure 11:
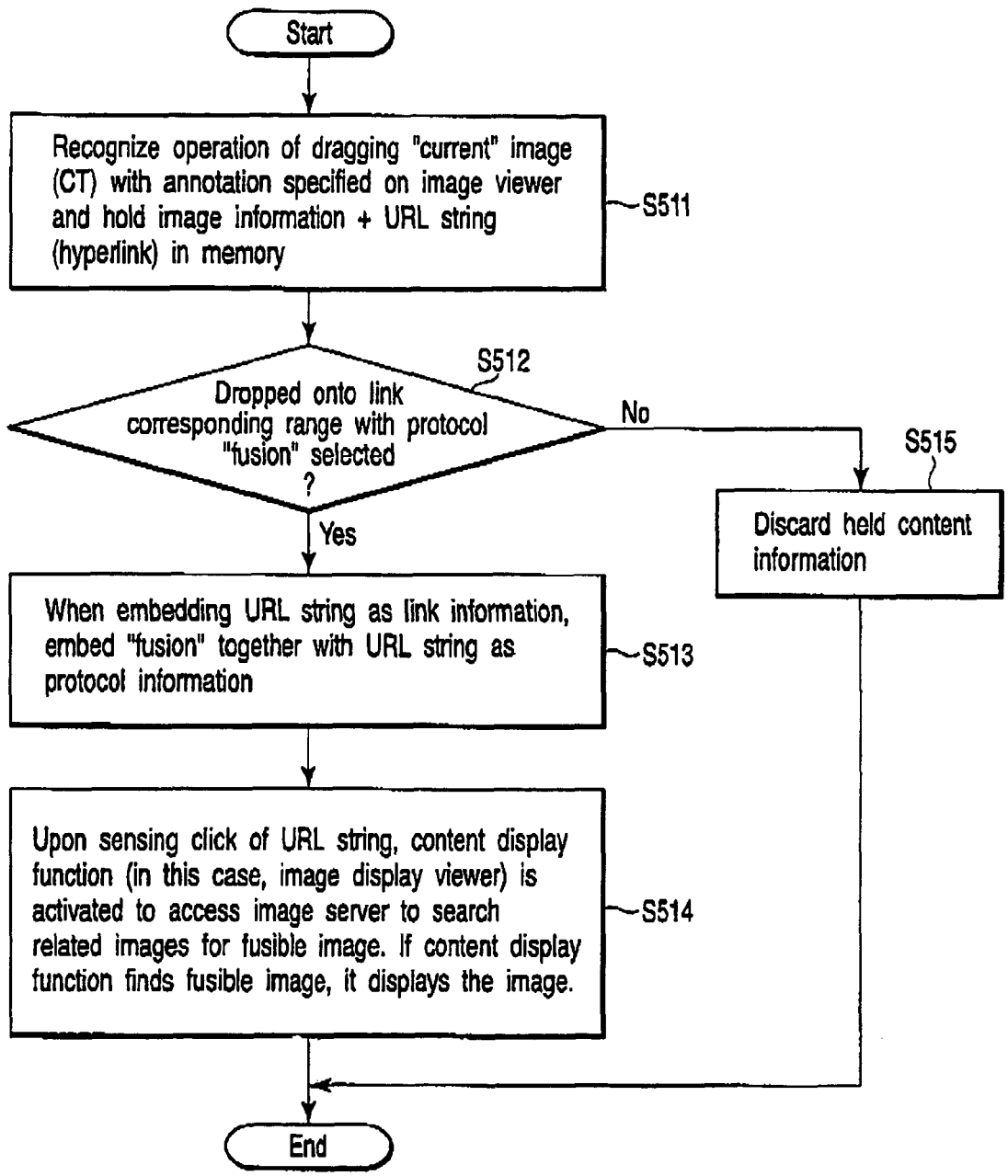
FIG. 11 is a flowchart showing a process procedure in Example 5 in which the medical report producing apparatus embeds protocol information.

FIG. 11 shows a process procedure in Example 5. In FIG. 11, first, the "current" image (CT) with an annotation is specified on the image viewer and dragged to the client viewer. The client viewer application then recognizes the dragged image and holds the image information and URL string (hyperlink) in the memory (S511). The client report application then determines whether or not the contents have been dropped onto the link corresponding range with a protocol "fusion" selected (S512). If the contents have been dropped under this condition, the client report application, when embedding the URL string as link information, additionally embeds the "fusion" as protocol information (S513). A click of the URL string allows the client report application to activate a content display function (in this case, the image display viewer), which then accesses the report apparatus and server to search the related images for a fusible image. If the content display function detects any fusible image, it displays that image (S514). In step S512, if the drop process has not been executed, the client report application discards the held content information (S515) to finish the series of processing operations.

An example of a URL string with the protocol information is "http://[server host name]/Dlink/ins.php?ins=1.2.3&Ser=4.5.6&stu=7.8.9&Mod=MR&StuDat=yyyymmdd&PatID=abcde&Param=XXXXXXX, Fusion".

Alternatively, as is understood from FIG. 22, described later, even if a URL string such as "http://[server host name]/Dlink/ins.php?ins=1.2.3&Ser=4.5.6&stu=7.8.9&Mod=MR&StuDat=yyyymmdd&PatID=abcde&Param=XXXXXXX" has been dragged, candidates for the protocol may be displayed to the user so that the user can select one of them or may be automatically added by default. Then, the above USL string may be considered to be "http://[server host name]/Dlink/ins.php?ins=1.2.3&Ser=4.5.6&stu=7.8.9&Mod=MR&StuDat=yyyymmdd&PatID=abcde&Param=XXXXXXX, A" to operate the corresponding protocol. In this case, a display form "7" (see FIG. 22) is selected for "7" in accordance with a priority protocol.

EXAMPLE 6

The apparatus determines whether or not the image or the string in the hypertext contains particular characters, for example, "patient's condition". If the image or string contains these characters, a waveform or specimen information is automatically displayed as the patient's information.

Figure 12:
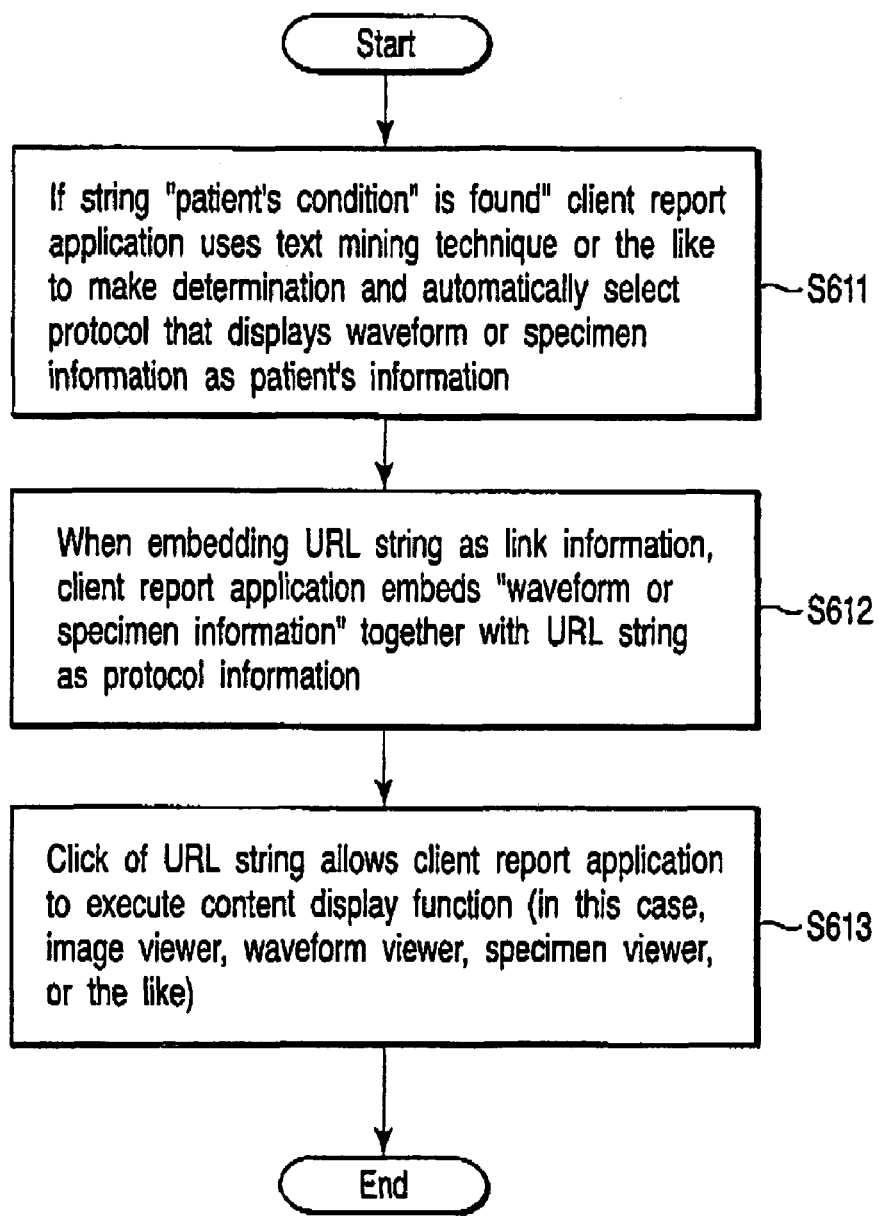
FIG. 12 is a flowchart showing a process procedure in Example 6 in which the medical report producing apparatus embeds protocol information.

FIG. 12 shows a process procedure in Example 6. In FIG. 12, first, if the string "patient's condition" is found, the client report application uses the text mining technique or the like to make determination. The client report application further automatically selects a protocol that displays a waveform or specimen information as the patient's information (S611). Then, when embedding the URL string as link information, the client report application additionally embeds the "waveform or specimen information" as protocol information (S612). A click of the URL string allows the client report application to display an image from the link destination through a content display function (in this case, the image display viewer, a waveform viewer, a specimen viewer, or the like).

An example of a URL string with the protocol information is "http://[server host name]/Dlink/ ins.php?ins=1.2.3&Ser=4.5.6&stu=7.8.9&Mod=M R&StuDat=yyyymmdd&PatID=abcde&Param= XXXXXXX, Waveform or specimen information". Further, this protocol specification parameter may be used to call and display the waveform viewer or specimen viewer (application that displays information on a specimen). This makes it possible to operate the protocol in the same manner if the following URL is simultaneously clicked: "http://[server host name]/HAKEIlink/ins. php?ins=1.2.3&Ser=4.5.6&stu=7.8.9&M od=MR&StuDat=yyyymmdd&PatID=abcde&Param= XXXXXXX" or "http://[server host name]/KENTAIlink/ ins.php?ins=1.2.3&Ser=4.5.6&stu=7.8.9& Mod=MR&StuDat=yyyymmdd&PatID=abcde&Param= XXXXXXX".

Description will be given of FIGS. 13 to 21 showing examples of displays based on the above protocols.

Figure 13:
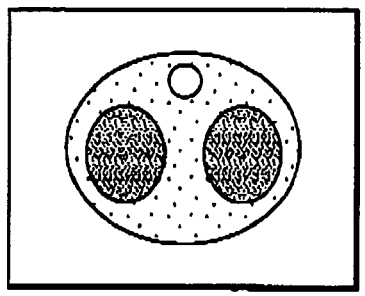
FIG. 13 is a diagram showing an example of a hyperlink image displayed when a hyperlink text is clicked.

FIG. 13 shows an example in which clicking a hyperlink text allows one pure image (or more images) to be displayed as a hyperlink image.

Figure 14:
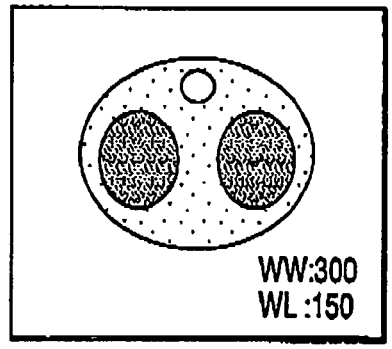
FIG. 14 is a diagram showing an example of the hyperlink image displayed when the hyperlink text is clicked.

FIG. 14 shows an example in which clicking the hyperlink text allows one image (or more images) to be displayed under a WW/WL (Window Width/Window Level) condition as a hyperlink image.

Figure 15:
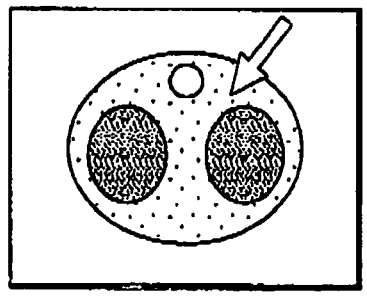
FIG. 15 is a diagram showing an example of the hyperlink image displayed when the hyperlink text is clicked.

FIG. 15 shows an example in which clicking the hyperlink text allows one image (or more images) with an annotation to be displayed as a hyperlink image.

FIG. 16 shows an example in which clicking the hyperlink text allows a MPR (Multi-Planar Reconstruction) coronal sectional image (or saggital sectional image) to be displayed next to the one image (or more images) saved as a hyperlink. Alternatively, a stack display may be provided or no images may be displayed. Alternatively, any of these displays may be selected.

Figure 17:
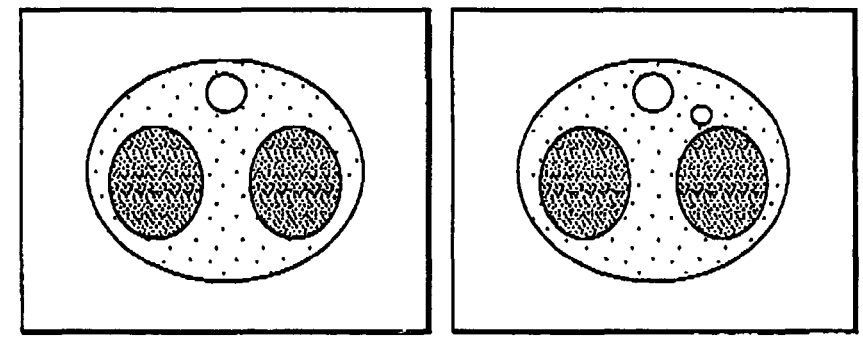
FIG. 17 is a diagram showing an example of the hyperlink image displayed when the hyperlink text is clicked.

FIG. 17 shows an example in which clicking the hyperlink text allows an image related to the one image (or more images) saved as a hyperlink to be displayed so that the last image is displayed next to the current image. Actually, the display of the related image may be limited depending on the number of links. For example, it is possible to set the display condition that "a specified display is provided if only one hyperlink is attached to the report". It is also possible to set the condition that "the specified display is not provided if N links are set up".

Figure 18:
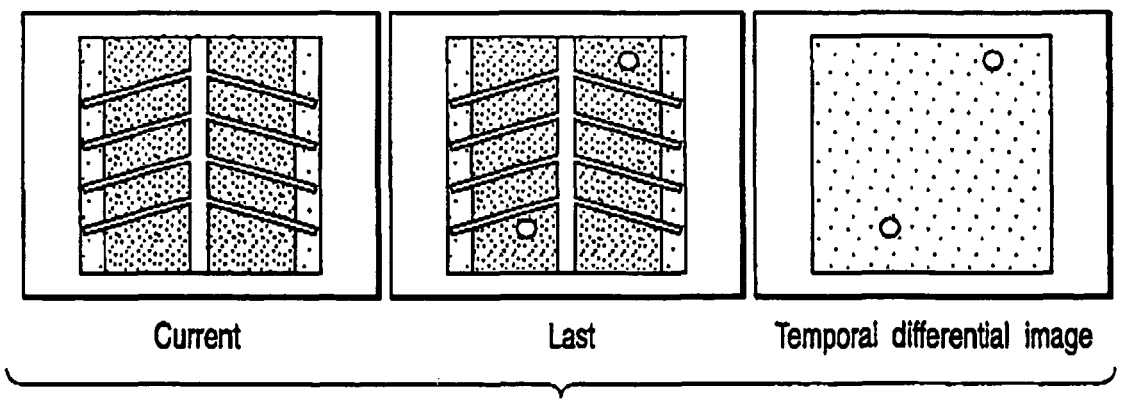
FIG. 18 is a diagram showing an example of the hyperlink image displayed when the hyperlink text is clicked.

FIG. 18 shows an example in which clicking the hyperlink text allows one image (or more images) (current image) to be displayed together with a temporal differential image. Settings may be made to determine whether or not to display the images.

Figure 19:
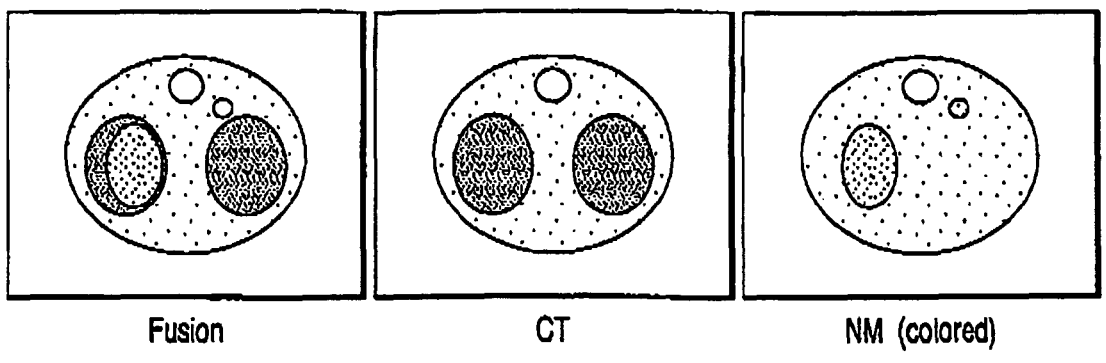
FIG. 19 is a diagram showing an example of the hyperlink image displayed when the hyperlink text is clicked.

FIG. 19 shows an example in which clicking the hyperlink text allows one fused (integrated) image (or more fused (integrated) images) saved as a hyperlink to be displayed together with an image in the original form, for example, a CT (Computed Tomography) or MR (Magnet Resonance) image, and an original functional image, for example, an NM (Nuclear Medicine) image. Of course, the images may be displayed in the opposite manner. A CT image may be displayed before a related fused and NM images. Settings may be made to determine whether or not to display the images.

Figure 20:
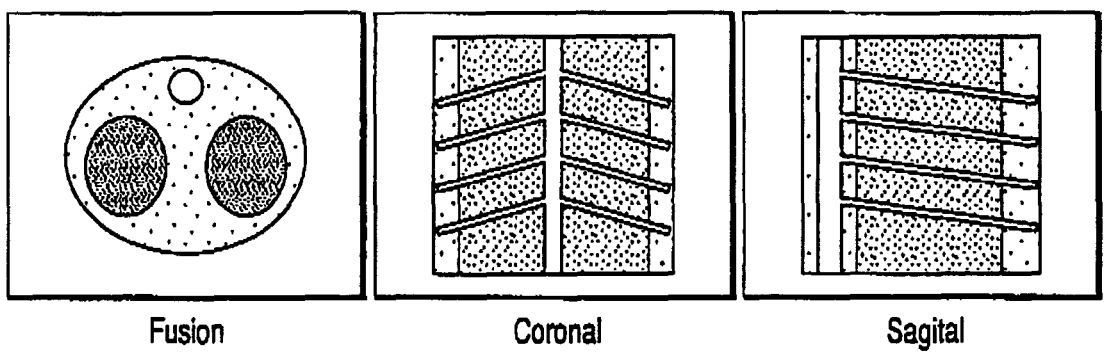
FIG. 20 is a diagram showing an example of the hyperlink image displayed when the hyperlink text is clicked.

FIG. 20 shows an example (in this example, MIP (Maximum Intensity Projection) images are displayed) in which clicking the hyperlink text allows one axial sectional image (or more axial sectional images) saved as a hyperlink to be displayed together with a coronal sectional image (MPR (Multi-Planar Reconstruction), MIP, or MINIP (Minimum Intensity Projection) image, or the like) and a saggital sectional image (MPR, MIP, or MinIP image, or the like).

Figure 21:
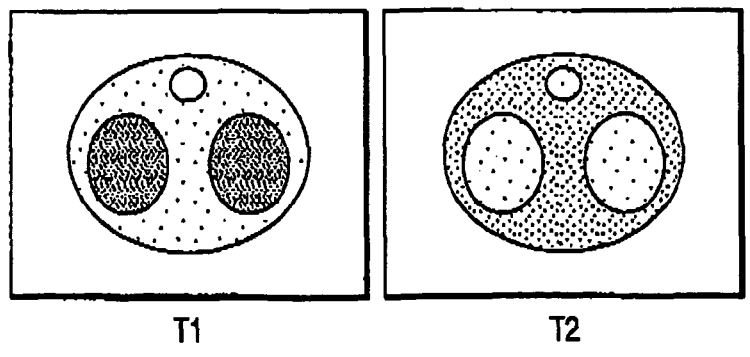
FIG. 21 is a diagram showing an example of the hyperlink image displayed when the hyperlink text is clicked.

FIG. 21 shows an example in which clicking the hyperlink text allows one MR image (or more MR images) taken at T1 (vertical relaxation time) saved as a hyperlink to be displayed next to an image taken at T2 (horizontal relaxation time). If the T2 image has already been displayed, the T1 image is additionally displayed.

The above display examples may be combined together so that selectable candidates are finally displayed as thumbnails or the like to allow the user to select any of them.

FIG. 22 is a table showing the optimum protocol selection logic that allows the optimum protocol to be automatically selected in order to link contents together. Key image statuses A to F show conditions for a hyperlinked image including reconstruction process, modality, imaging site, imaging condition, use of contrast, and related image display candidates (comparison protocol numbers 1 to 5). FIG. 22 also shows the relationship between priority display protocols and Examples 1 to 6 and FIGS. 13 to 21.

The comparison protocol numbers are shown in another table in FIG. 23. Specifically, comparison protocol numbers 1 to 14 shown in FIG. 23 are set for comparison protocol numbers −1 to −5 depending on the key image statuses A to F (for example, the number 1 is set for the comparison protocol number −1 under the conditions for the image A), so as to operate the corresponding comparison protocols. According to the table, for example, the comparison protocol number −1 and the conditions "CT", "chest", and "lung field" determine that the last CT image without any contrast be selected and displayed, For a comparison process, the display direction and position remain unchanged.

If only one candidate for related image display is available, it may be displayed as it is or the display may be turned off. If a large number of candidates for related image display are available, the comparison protocol number 1 may be set by default or the display may be turned off.

Figure 24:
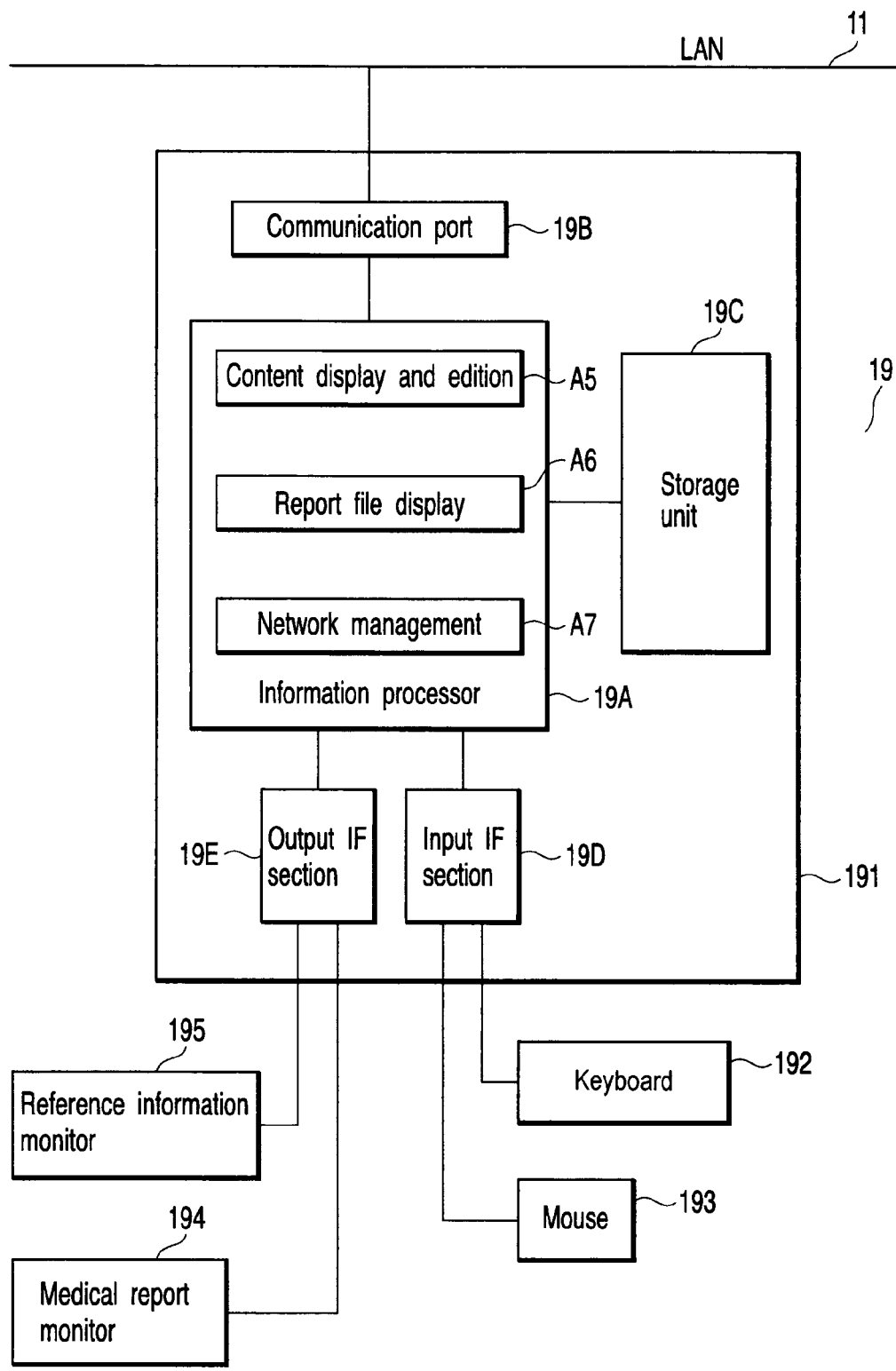
FIG. 24 is a block diagram showing an embodiment of a medical report viewer apparatus according to the present invention.

The viewer apparatus 19 makes it possible to view a medial report file produced by the medical report producing apparatus configured as described above. As shown in FIG. 24, the viewer apparatus 19 has basically the same configuration as that of the medical report producing apparatus shown in FIGS. 2 and 3 and comprises a workstation apparatus 191 connected to the network 11 (this also applies to the viewer apparatus 20). A keyboard 192 and a mouse 193 are connected to the workstation apparatus 191, which comprises a report monitor device 194 and a reference information monitor device 195 as display devices. The reference information monitor device 195 is desirably a multidisplay that enables much reference information to be monitored at a time. However, a single display can be used to provide a screen display in multiwindow form.

Here, an apparatus dedicated for report reference is assumed, but a terminal device of an electronic medical report system or any other reference apparatus may be utilized.

The workstation apparatus 191 comprises an information processor 19A, a communication port 19B, a storage unit 19C in which information is stored for operations, an input interface 19D that receives instruction information corresponding to an input operation provided via the keyboard 192 and mouse 193, and an output interface section 19E that outputs monitor display information to a report monitor device 194 and a reference information monitor device 195.

The information processor 19A reads reference contents linked to a medical report file and a finding section, directly from the medical report producing apparatus 18 through the communication port 19B or via the medical information server 12. The reference contents are then stored in the storage unit 19C. The information processor 19A comprises, as applications, a content displaying and editing program A5 that monitors the reference contents to perform editing operations such as enlargement, reduction, and clipping, a report file displaying program A6 that displays an electronic file for a medical report, and a network managing program A7. The information processor 19A selects and executes any of these programs in response to power-on and in accordance with the operator's instruction input.

When a medical report produced by the medical report producing apparatus 18 is displayed on the monitor 194 of the medical report referencing apparatus 19 configured as described above, a string (hyperlink text) to which the hyperlink for a finding section of the medical report is identified and displayed. Thus, specifying the string allows linked address information to be acquired, so that the contents at the address are read and displayed on the monitor 145. On this occasion, if any protocol is embedded in the hyperlink, the apparatus executes, for example, selective display in accordance with the protocol with the conditions varying depending on the status of the linked key image; the conditions include reconstruction process, modality, imaging site, imaging condition, use of contrast, and related image display candidates.

Further, enabling the display of a link list makes it possible to effectively utilize the display space. If a link is attached to a reduced image in the link list, specifying the reduced image enables the corresponding contents to be displayed on the monitor 145.

If editing parameter information is added to the linked address information, contents read using the parameter information is edited and displayed. For example, if production of reference contents involves an editing operation such as enlargement, reduction, marking, or clipping, it can be reproduced during viewing. This enables the viewer to easily understand the medical specialist's intention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical report producing apparatus which produces an electronic file for a trace reading report on one or more medical images to be trace-read, the apparatus comprising:
   means for producing the electronic file for the medical report on the basis of information input in accordance with an operation of an operator;
   means for displaying a production screen for the medical report produced by the information processing means; and
   means for selectively displaying content including at least one of a medical image, a past medical report, and an information file, the content being referenced in order to produce the medical report,
   the means for producing including
      means for inputting a string to a finding section of the medical report;
      means for identifying a link corresponding range in the string in the finding section;
      means for acquiring address information of the content in response to an input for designating the content displayed on the second display means, and linking the address information to information indicating the string in the link corresponding range to produce a hyperlink text, the input for designating the content being performed by a drag and drop operation;
      means for selecting a protocol from among a plurality of predefined protocols, in accordance with an instruction input of the operator, the protocol including a macrofunction configured to be executed when a hyperlink corresponding to the hyperlink text is activated; and
      means for embedding, in the hyperlink text in response to the drag and drop operation, protocol information indicating the selected protocol.

2. The medical report producing apparatus according to claim 1, wherein the plurality of predefined protocols are pre-registered, and the means for selecting specifies and inputs one of the protocols so that the specified protocol is contained in the hyperlink text.

3. The medical report producing apparatus according to claim 1, wherein the plurality of predefined protocols include at least one of a protocol which changes a display operation depending on contents of linked content individual information, a protocol which searches for and displays related contents other than the linked content, and a protocol which checks a string of the hyperlink text itself.

4. The medical report producing apparatus according to claim 1, wherein the means for acquiring comprises means for grouping procedures and image processing operations performed for the trace reading determination, in functional blocks, selects any of the functional blocks, and arranges the selected blocks in accordance with a time series.

5. The medical report producing apparatus according to claim 1, further comprising means for automatically reading and displaying two contents using the protocol when a "current" content and a "last" content are linked to the report and a user clicks on either of two hyperlinks.

6. The medical report producing apparatus according to claim 1, wherein the protocol automatically searches for and displays a series including the specified content.

7. The medical report producing apparatus according to claim 1, wherein when the linked content relates to a particular modality and a particular site, the protocol searches for past contents, and if any past content is present, produces and automatically displaces a temporal differential content.

8. The medical report producing apparatus according to claim 1, wherein the protocol determines whether or not the linked content contains any annotation information, and if the linked content contains annotation information, automatically reconstructs and displays a related cross section at a location corresponding to the annotation information.

9. The medical report producing apparatus according to claim 1, wherein the protocol determines whether or not the linked content has any integrable data, and if the linked content has integrable data, provides an integrated display.

10. The medical report producing apparatus according to claim 1, wherein the protocol determines whether or not the string to be linked has a particular character, and if the string has the character, automatically displays particular information.

11. The apparatus according to claim 1, further comprising means for preparing appropriate protocols in a table for respective conditions set for the medical images, wherein one of the appropriate protocols, which corresponds to one of the conditions, is automatically associated when the one condition is designated.

12. A method implemented by a processor programmed as a medical report producing apparatus for producing an electronic file for a medical report on one or more medical images to be trace-read, the method comprising:

causing, by the medical report producing apparatus, a production screen for a medical report to be displayed on the basis of the electronic file and causing selective display of content including one of a medical image, a past medical report, and an information file that are referenced in order to produce the medical report;

inserting a string input by an operation of an operator into a finding section of the medical report;

identifying a link corresponding range in the string in the finding section;

acquiring address information of the content in response to an input for designating the content displayed, and linking the address information to information indicating the string in the link corresponding range to produce a hyperlink text, the input for designating the content being performed by a drag and drop operation;

selecting a protocol from among a plurality of predefined protocols, in accordance with an instruction input of the operator, the protocol including a macrofunction configured to be executed when a hyperlink corresponding to the hyperlink text is activated; and embedding, in the hyperlink text in response to the drag and drop operation, protocol information indicating the selected protocol.

13. The method for producing a medical report according to claim 12, wherein the plurality of predefined protocols are pre-registered, and one of the protocols is specified and input so that the specified protocol is contained in the hyperlink text.

14. The method for producing a medical report according to claim 12, wherein the plurality of predefined protocols include at least one of a protocol which changes a display operation depending on contents of linked content individual information, a protocol which searches for and displays related contents other than the linked content, and a protocol which checks a string of the hyperlink text itself.

15. The method for producing a medical report according to claim 12, wherein the linking step comprises protocol production support involving grouping procedures and image processing operations performed for the trace reading determination, in functional blocks, selecting any of the functional blocks, and arranging the selected blocks in accordance with a time series.

16. The method for producing a medical report according to claim 12, further comprising clicking either of two hyperlink displays, which allows the protocol to automatically read and display two contents, when a current content and a last content are linked to the medical report.

17. The method for producing a medical report according to claim 12, wherein the protocol automatically searches for and displays a series including the specified content.

18. The method for producing a medical report according to claim 12, wherein when the linked content relates to a particular modality and a particular site, the protocol searches for past contents, and if any past content is present, produces and automatically displaces a temporal differential content.

19. The method for producing a medical report according to claim 12, wherein the protocol determines whether or not the linked content contains any annotation information, and if the linked content contains annotation information, automatically reconstructs and displays a related cross section at a location corresponding to the annotation information.

20. The method for producing a medical report according to claim 12, wherein the protocol determines whether or not the linked content has any integrable data, and if the linked content has integrable data, provides an integrated display.

21. The method for producing a medical report according to claim 12, wherein the protocol determines whether or not the string to be linked has a particular character, and if the string has the character, automatically displays particular information.

22. The method according to claim 12, further comprising preparing appropriate protocols in a table for respective conditions set for the medical images, and automatically associating one of the appropriate protocols, which corresponds to one of the conditions, when the one condition is designated.

* * * * *